US006736010B1

(12) United States Patent
Muller et al.

(10) Patent No.: US 6,736,010 B1
(45) Date of Patent: May 18, 2004

(54) METHOD AND DEVICE FOR COUNTING INCLUSIONS IN A LIQUID METAL BATH WITH ULTRASOUNDS

(75) Inventors: Jean Muller, Ariege (FR); Pierre Le Brun, Saint Jean de Soudain (FR); Thierry Odievre, Coublevie (FR)

(73) Assignees: Pechiney Rhenalu, Paris (FR); Aluminium Pechiney, Paris Cedex (FR)

(*) Notice: Subject to any disclaimer, the term of this patent is extended or adjusted under 35 U.S.C. 154(b) by 0 days.

(21) Appl. No.: 10/019,449

(22) PCT Filed: Jul. 5, 2000

(86) PCT No.: PCT/FR00/01927

§ 371 (c)(1),
(2), (4) Date: Apr. 25, 2002

(87) PCT Pub. No.: WO01/04620

PCT Pub. Date: Jan. 18, 2001

(30) Foreign Application Priority Data

Jul. 9, 1999 (FR) .............................. 99 09123

(51) Int. Cl.$^7$ .............................................. G01N 29/02
(52) U.S. Cl. ........................... 73/600; 73/865.5; 73/644
(58) Field of Search .................... 73/598, 600, 627, 73/644, 865.5

(56) References Cited

U.S. PATENT DOCUMENTS

| 3,444,726 A | | 1/1966 | Young et al. |
| 3,802,271 A | * | 4/1974 | Bertelson ................ 73/61.75 |
| 4,130,018 A | * | 12/1978 | Adams et al. ................ 73/644 |
| 4,261,197 A | | 4/1981 | Mansfield |
| 4,287,755 A | | 9/1981 | Mansfield |
| 4,527,420 A | | 7/1985 | Foote |
| 4,563,895 A | | 1/1986 | Eckert |
| 4,662,215 A | | 5/1987 | Eckert |
| 4,739,662 A | | 4/1988 | Foote |
| 4,770,699 A | | 9/1988 | Mountford |
| 4,843,866 A | | 7/1989 | Madsen et al. |
| 4,981,045 A | | 1/1991 | Mountford |
| 5,121,629 A | | 6/1992 | Alba |
| 5,604,301 A | | 2/1997 | Mountford et al. |
| 5,708,209 A | | 1/1998 | Stiffler et al. |
| 5,828,274 A | | 10/1998 | Jen et al. |

FOREIGN PATENT DOCUMENTS

| DE | 4445494 | | 6/1996 |
| GB | 1419118 | | 9/1975 |
| GB | 2255408 | | 4/1992 |
| GB | 2255408 | * | 11/1992 |
| GB | 2257786 | | 1/1993 |
| WO | 98/46987 | | 10/1998 |

* cited by examiner

Primary Examiner—Hezron Williams
Assistant Examiner—Nashmiya Fayyaz
(74) Attorney, Agent, or Firm—Dennison, Schultz & Dougherty

(57) ABSTRACT

Process and apparatus for displaying, measuring the size of and counting individual inclusions in suspension in moving liquid metal using an ultrasound sensor including emission and reception devices. Using the emission device, a series of ultrasound beam pulses is emitted within the liquid metal, and echoes reflected by the inclusions are received using the reception device. The reflected echoes are successively acquired and processed, and displayed as images which are analyzed to count and measure the diameter of inclusions. The sensor is calibrated by selectively placing in a path defined by the beam pulses at least one control reflector having predetermined dimensions and a geometry stable over time, successively acquiring and processing reflected echoes from the control reflector, displaying the reflected echoes from the control reflector as images, and analyzing the control reflector echo images to determine a relationship between amplitude of the images and the control reflector dimensions.

8 Claims, 2 Drawing Sheets

METHOD AND DEVICE FOR COUNTING INCLUSIONS IN A LIQUID METAL BATH WITH ULTRASOUNDS

FIELD OF THE INVENTION

This invention relates to an improved ultrasound process and device for counting liquid and/or solid inclusions present in a liquid metal flow usually in a vessel or better in a trough, and for measuring their size. The invention is particularly applicable to aluminium, magnesium or their alloys.

DESCRIPTION OF RELATED ART

It is extremely important to be able to precisely control the quality of inclusions when casting liquid aluminium; the quality of thin plates and the proportion put into scrap depends on this quality of inclusions, particularly for plates made for the manufacture of closed drink or aerosol can receptacles.

Generally, the inclusion quality of a liquid metal is determined using the number density and size of inclusions contained in the liquid metal.

Characterization methods usually involve taking samples of at most about 0.01% of the liquid metal. Considering that the number density of the inclusions to be measured is low (of the order of 1 ppm), that there are few large inclusions, and that the latter are the most harmful inclusions when a thin plate is required, it can be seen that, with this type of sampling method, there is a risk that the results obtained may not be really representative and that the probability of seeing the said inclusions is very low.

For instance, there is one known method called Podfa (Porous Disk Filtration of Aluminium) that essentially consists of discontinuously taking off a sample of liquid metal, filtering it and analysing the recovered inclusions; but this method simply provides an approximate idea about the size and number of inclusions. Another method called LIMCA (Liquid Metal Cleanliness Analysis) is also known that essentially consists of continuously sampling the liquid metal through a small orifice and measuring the variation in the resistance of the liquid metal at each passage of an inclusion; but this method does not work for large inclusions (in other words inclusions larger than about 100 $\mu$m). Therefore it appears difficult to use one of these methods to measure the amount of progress that can still be done towards eliminating inclusions, and particularly large inclusions.

The inclusion quality may also be evaluated by measurements made in situ and continuously using ultrasounds; this type of method can sample up to 5% of the liquid metal, particularly when the metal is circulating in a trough.

For example, U.S. Pat. No. 4,981,045 (University of Toronto) describes an ultrasound probe and process used to test for the presence of defects, and particularly inclusions, in a liquid metal crucible. This probe comprises a delay line forming the link between the emitter/receiver piezoelectric crystal and the liquid metal that can melt in the latter; for that purpose it is usually based on the same metal as the metal to be analyzed and is cooled to prevent it from being completely destroyed. This ensures acoustic continuity between the said delay line and the said liquid metal.

The method essentially consists of immersing two probes in the said liquid metal through the free end of their delay line; wave streams are sent regularly and reflected signals are analysed. A large peak is detected due to the echo of ultrasounds on the wall of the crucible; an average content of inclusions in the metal fraction being analysed is determined from the attenuation of this peak; this peak has to be calibrated in advance using a metal considered to be pure.

It is also mentioned that the number of inclusions at a certain depth in the tested volume can be counted by the probes, by counting the number of peaks due to reflections of signal on inclusions using a computer, and that it is difficult to make measurements for all the metal contained in the crucible. This type of method is not calibrated and counting is not very precise.

U.S. Pat. No. 5,708,209 (Alcoa) also describes the use of a special type of emitting and receiving probes with meltable delay lines to detect particles present in a liquid metal. The comments given above are applicable.

These processes are only capable of analysing a restricted volume of liquid metal, and usually only provide approximate global information about inclusions so that it is only possible to say if the liquid metal is clean or dirty, and do not provide any precise information about the number and size of inclusions.

Attempts have been made to obtain information about the size of inclusions by introducing particles of a known size into supposedly pure liquid aluminium and comparing the count obtained with the count made on the metal to be analysed. This type of method cannot be used industrially. It is not realistic to plan to use pure metal in an industrial installation without the risk of it getting dirty, and consequently the calibration measurement would be biased; furthermore, the introduction of particles could pollute and severely disturb the industrial manufacturing cycle.

In order to provide more precise information about the size, particles would have to be perfectly spherical and the size of particles contained in the size grading selection added into the pure metal would have to be homogeneous, which is not normally the case. Furthermore, particles can create shadows and agglomerate together. All this makes the method unreliable and difficult to perform.

Thus, the applicant searched for a reliable method capable of providing significant results for analysing the quality of inclusions in a liquid metal. In particular, the applicant attempted to find a method to count and give precise information about the size of inclusions, particularly large inclusions (typically larger than 50 $\mu$m), even in small quantities, the method being calibrated and the accuracy of which can be checked periodically without modifying the progress of industrial operations.

SUMMARY OF THE INVENTION

The invention is a process for displaying, measuring the size and making an individual count of inclusions in suspension in a moving liquid metal, using a sensor comprising at least one means of emitting a series of ultrasound beam pulses within the said liquid metal, at least one means of receiving echoes reflected from the said inclusions and their accessories, characterized in that it comprises a step for calibration of the sensor response, the said step using at least one control reflector with known dimensions and stable with time, successive steps to acquire and process reflected echoes, a display step, for example a B scan type display as will be described later, and an image analysis step to count and measure the diameter of inclusions.

In other words, the process according to the invention comprises emitting a series of ultrasound beam pulses within the said liquid metal by means of the said sensor, reception of the echoes reflected by the said inclusions using the said sensor, a step for calibration of the response of the said sensor, successive steps for the acquisition and processing of the reflected echoes, a display step, for example a B scan type display, and an image analysis step to count and measure the diameter of inclusions.

Although the process can be applied in any type of liquid metal processing vessel, it is particularly attractive to use it in troughs in which the said metal is circulating and where it can be used to continuously analyse a large proportion of the flow or the entire flow.

For the calibration, it is important that there should be at least one and preferably a plurality of control reflectors with individually known sizes, that are stable with a known and controlled geometry giving an echo that can be reproduced in time. A plurality of reflectors with different sizes are used in the preferred embodiment of the invention. It is thus possible to set up a calibration curve for the response of the sensor giving the amplitude of the echo signal as a function of the said dimensions of the control reflectors and extrapolating the curve for small inclusions.

Reflectors may advantageously consist of the straight section of one or several rods with a calibrated (and therefore known) diameter. The rods are preferably inert, in other words they are preferably made of a material that is inert to the liquid metal, such as a refractory ceramic. The rods are usually fixed on a removable support, and are typically immersed in the sensor field in the liquid metal during the calibration step, and are then taken out of the sensor field during liquid metal analysis sequences; they can be put back in periodically to check the said calibration. It is usually sufficient if only one end of the rod(s) is (are) immersed in the sensor field. The end of the rod(s) immersed in the sensor field (and more precisely in the focal spot formed by the intersection of ultrasound beams emitted and received by the said emission and reception means), which may have different geometries, advantageously has a flat surface to give optimum reflection. This end is typically the top end of the rod when the rod is placed vertically. Preferably, a plurality of rods with different diameters are used, so that an effective calibration curve for the sensor can be defined based on the size of the inclusions. Other types of control reflectors may be used, for example spheres, cones or calibrated cavities fixed to a support.

After the sensor response, curve as a function of the diameter has been determined, it can be extrapolated, for example when the diameter of the smallest control reflectors is 100 $\mu$m, for smaller values of the diameter so that the size of smaller inclusions down to 50 $\mu$m or less can be measured pith good precision.

Control reflectors are typically made of a refractory material and are inert with respect to liquid metal, usually alumina in the case of aluminium; they may advantageously be coated with a deposit (for example titanium) to guarantee good wetting by the liquid metal.

The signal display step may be done by putting successive reflected signals together, this representation being known as a B-scan type echography. A C-scan type method could be used.

It can be seen that if a procedure according to the invention is used, calibration is easy to perform, does not pollute the liquid metal and is rigorous, taking account of the exact and individual knowledge about the diameter of control reflectors and due to the fact that the calibration may be done easily at any time as a check without affecting production. Thus, the precision of the inclusion size measurement is guaranteed.

Another purpose of the invention is a device to implement the process for analysis of inclusions contained in a liquid metal flow according to the invention. This device is characterized in that it comprises an ultrasound sensor comprising at least one emission means 1 such as an emitting probe, at least one reception means 2 such as a reception probe, and their accessories, at least one control reflector, a device for acquisition and processing of reflected ultrasound echoes, a device for displaying the said inclusions and an image analysis device to count and measure the diameter of the said inclusions.

DESCRIPTION OF THE PREFERRED EMBODIMENT

Figure 1:
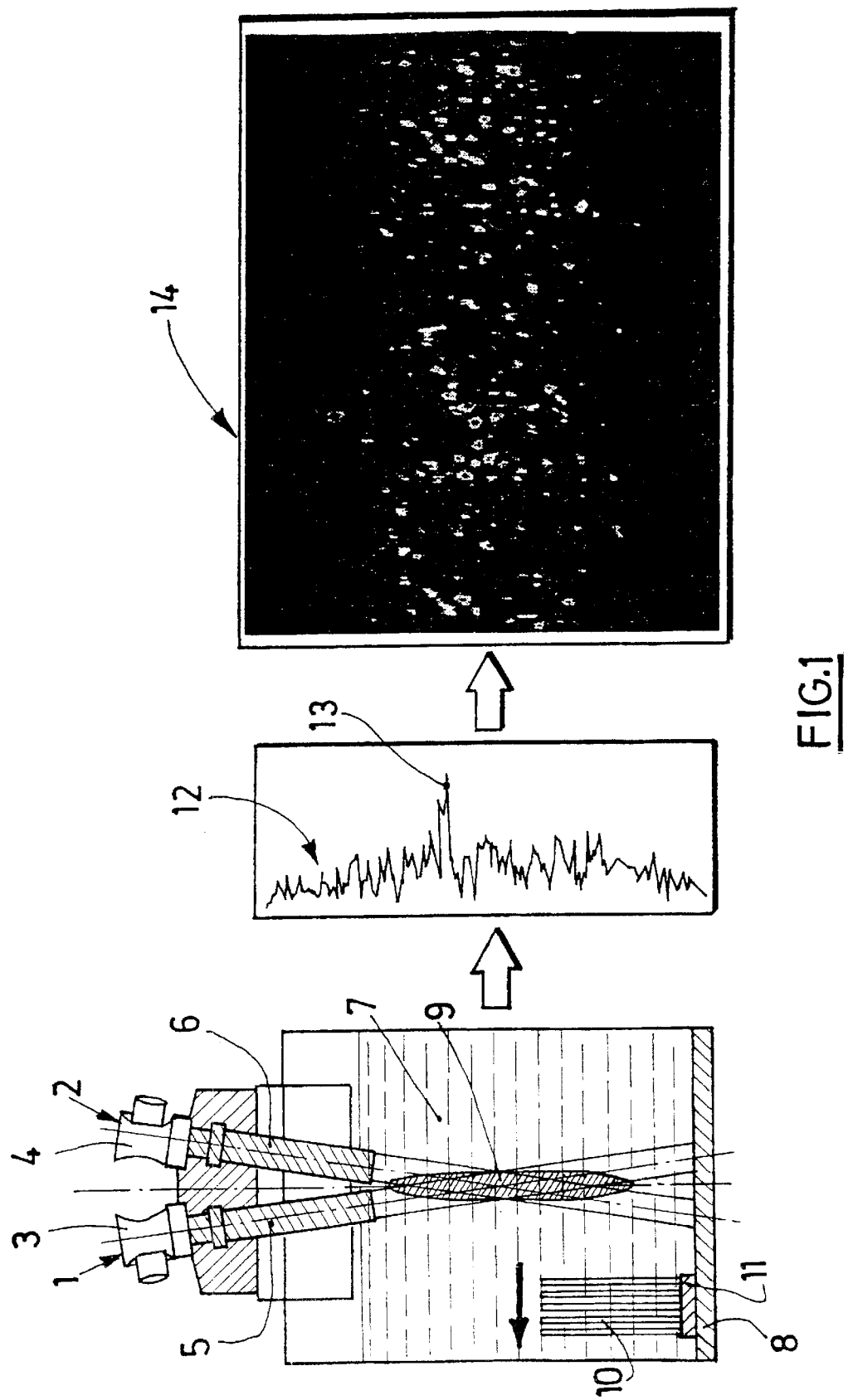
FIG. 1 diagrammatically shows the invention.

FIG. 1 shows that the sensor essentially comprises an emission means 1 and a reception means 2. In the preferred embodiment of the invention, the said means of emitting the said succession of ultrasound beam pulses, or "emission means", is typically a probe, called the emitting probe, that is capable of emitting the said pulses, and the said means of receiving the said echoes reflected by the said inclusions, called the "reception means", is typically a probe called the "receiving probe" capable of receiving the said echoes. Separation of the emission and reception functions is a means of improving the sensitivity of the sensor. However, without going outside the scope of the invention, it would be possible to put the said emission and reception means, or a part of the said means, into one probe called the "emitter/receiver" probe capable of carrying out emission and reception functions. If more than one emission means and/or more than one reception means is used, it is also possible to combine probes with a single function (emission or reception) and emitting/receiving probes.

Each emission or reception means comprises at least one ultrasound translation element 3, 4 (for example comprising piezoelectric type transducers) prolonged by a delay line 5, 6 making the link between the translator 3, 4 and the liquid metal flow 7 circulating in a trough 8 along the direction of the arrow.

The characteristics of the delay line are good resistance to temperature, good chemical inertness to the liquid metal, good transparency to ultrasounds and wettability by the said liquid metal so that the signal can be emitted with the lowest possible losses. Materials suitable for this application are generally metals such as Fe, Al, Zr, Ti, Nb or ceramics such as TiB2, quartz, carbide, nitrite, oxycarbide, oxycarbonitride (SiAlON). When the delay line is made of the same metal as the analysed liquid metal, it should be cooled to prevent it from being destroyed.

The intersection of the emitted and received beams emitted by the emission means (1) and received by the reception means (2) forms a focal spot (9) which is the volume within which the calibration is made and inclusions are analysed. The focal spot may cover the entire depth of the liquid metal stream in the trough and its volume can then be up to 10% of the volume of the liquid circulating in the trough, or even more and possibly the total volume depending on the shape of the trough.

The control reflector in the figure comprises a set of inert refractory rods (10) with various known diameters, usually more than 100 $\mu$m; the said rods are typically vertical and fixed to a mobile support (11) placed on the bottom of the trough (8). During the calibration step or when carrying out periodic checks during measurement sequences, the support is moved so as to bring the rods (10) into the focal spot (9) and then to pull them out of the spot.

Successive ultrasound pulses are emitted using this device. The ultrasound frequency is usually chosen within the range 0.5 to 50 MHz, and preferably 5 to 50 MHz, which within the preferred range, corresponds to a typical particle detection limit ($\lambda/10$) of between 100 and 10 $\mu$m respectively. The pulse repetition frequency is typically about 1 kHz.

The signal acquisition and processing step is done by computer and the result is a diagram (12) for each pulse showing a noise background and peaks (13) corresponding to reflections on reflecting objects (inclusions and/or control reflectors (10)) located in the focal spot (9). When the said focal spot (9) occupies the entire height of the liquid metal stream, peaks will be observed corresponding to echoes from bottom of the trough.

Figure 2:
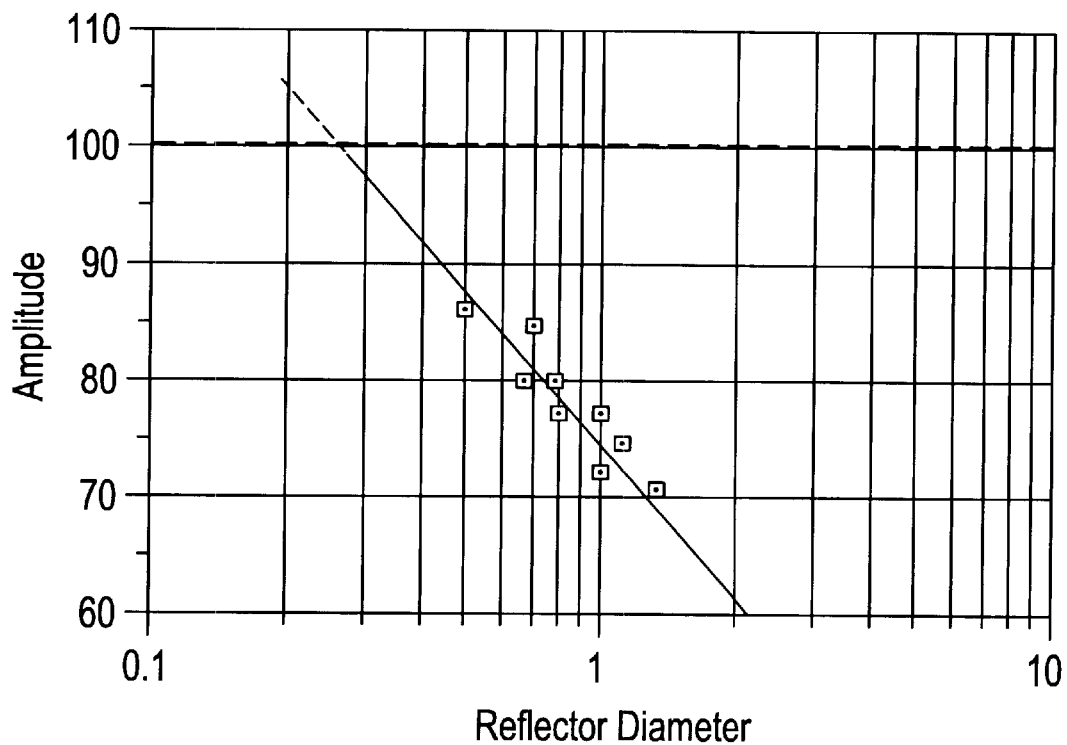
FIG. 2 contains an example of a calibration curve.

As we have already said, the amplitude of the echo signal obtained in this diagram varies with the diameter of the reflecting obstacle for a given ultrasound frequency. As an example, FIG. 2 shows a calibration curve obtained using control reflectors (10) with various diameters showing the amplitude of the received signal (the ordinate) as a function of the diameter of the reflecting obstacles (the abscissa). This curve facilitates extrapolation of small diameters if no calibration is available in this area.

The information corresponding to the successive diagrams (12) is then processed by computer in the display step using a B scan type representation to show an image (14) of the echoes of reflecting obstacles sliding at the speed of the liquid metal stream, on which the said echoes are shown by spots with an intensity related to the size of the said obstacles. After calibration of these spots using calibrated control reflectors (10), it can be seen that it is easy to precisely count and measure the diameter of inclusions using an image analysis.

EXAMPLE

A characterization was made on an experimental casting line and the quality of liquid metal produced by two furnaces was evaluated. One of the furnaces was clean, and the other was contaminated by inclusions. Table 1 contains the number of peaks corresponding to inclusions with equivalent sizes larger than 300 and 500 $\mu$m, as estimated from the probed volume (about 5% of the cast volume) and expressed as a number per kg.

TABLE 1

|  | Contaminated furnace | Clean furnace |
| --- | --- | --- |
| Inclusions with equivalent size larger than 300 $\mu$m | 0.40 | 0.03 |
| Inclusions with equivalent size larger than 500 $\mu$m | 0.12 | 0.00 |

Advantages of the Invention

The process is particularly useful for making a precise count of the largest inclusions, typically larger than 100 $\mu$m, which are usually present in small numbers and are therefore difficult to identify using other analysis methods, but which are the most harmful, and for determining their size.

This invention provides a useful method of analysing the entire flow of liquid metal circulating in a receptacle or a trough. All that is necessary is to have several emission and reception means, typically probes, with their delay line, side by side or staggered on opposite sides of the liquid metal flow, or to have a sensor with the same width as the said flow in which each emission and reception means comprises a multi-element translator comprising a plurality of contiguous piezoelectric transducers prolonged by a delay line also adapted to the flow width of the liquid metal. In all cases, this plurality of translators is associated with an electronic control for electronic scanning of the acoustic beam thus formed. Preferably, the said control can also be used to focus the acoustic beam. The entire liquid metal flow is analysed provided that the focal spot passes through the entire liquid metal stream in the vertical direction.

What is claimed is:

1. Process for displaying, measuring the size of and counting individual inclusions in suspension in moving liquid metal using an ultrasound sensor comprising emission and reception means, comprising the steps of:

emitting, using the emission means, a series of ultrasound beam pulses within said liquid metal, receiving, using the reception means, echoes reflected by said inclusions, successively acquiring and processing said reflected echoes, displaying said echoes as images, analyzing the images to count and measure the diameters of inclusions, and calibrating the sensor to measure inclusion size, comprising selectively placing in a path defined by the beam pulses at least one control reflector having predetermined dimensions and a geometry stable over time, successively acquiring and processing reflected echoes from the at least one control reflector, displaying the reflected echoes from the at least one control reflector as images, and analyzing the control reflector echo images to determine a relationship between amplitude of said control images and the control reflector dimensions.

2. Process according to claim 1, wherein said at least one control reflector is a rod.

3. Process according to claim 2, wherein said at least one control reflector has an end which is a flat surface.

4. Process according to claim 1, wherein the calibrating is carried out by introducing into the liquid metal a plurality of control reflectors that are inert with respect to the liquid metal, with calibrated diameters, in a focal spot formed by intersecting emitted and received ultrasound beams.

5. Process according to claim 4, wherein the plurality of control reflectors comprises a set of rods.

6. Process according to claim 5, wherein at least an end of the rods which is immersed in the liquid metal at the said focal spot has a flat surface.

7. Process according to claim 4, wherein said calibrating includes establishing a calibration curve of image amplitude vs. control reflector diameter.

8. Process according to claim 1, wherein the ultrasound beam pulses comprise ultrasound waves having a frequency between 0.5 and 50 MHz.

* * * * *